United States Patent
Sabelle et al.

(10) Patent No.: US 11,083,679 B2
(45) Date of Patent: Aug. 10, 2021

(54) USE OF SUBSTITUTED DIHYDROISOQUINOLINIUM SALTS FOR TREATING KERATIN MATERIALS, COMPOSITIONS AND IMPLEMENTATION PROCESSES

(71) Applicant: L'OREAL, Paris (FR)

(72) Inventors: Stéphane Sabelle, Aulnay-sous-Bois (FR); Aziz Fadli, Aulnay-sous-Bois (FR); Alexandra Charrier, Aulnay-sous-Bois (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/064,291

(22) PCT Filed: Dec. 23, 2016

(86) PCT No.: PCT/EP2016/082580
§ 371 (c)(1),
(2) Date: Jun. 20, 2018

(87) PCT Pub. No.: WO2017/109185
PCT Pub. Date: Jun. 29, 2017

(65) Prior Publication Data
US 2019/0008742 A1 Jan. 10, 2019

(30) Foreign Application Priority Data
Dec. 23, 2015 (FR) ........................ 1563276

(51) Int. Cl.
| A61K 8/49 | (2006.01) |
| C07D 217/10 | (2006.01) |
| C07D 217/14 | (2006.01) |
| A61Q 5/08 | (2006.01) |
| A61K 8/22 | (2006.01) |
| A61Q 5/10 | (2006.01) |

(52) U.S. Cl.
CPC .......... *A61K 8/4926* (2013.01); *A61K 8/22* (2013.01); *A61K 8/49* (2013.01); *A61Q 5/08* (2013.01); *C07D 217/10* (2013.01); *C07D 217/14* (2013.01); *A61Q 5/10* (2013.01)

(58) Field of Classification Search
CPC ...... C07D 217/10; C07D 217/14; A61Q 5/08; A61Q 5/10; A61K 8/4926; A61K 8/22; A61K 8/49
See application file for complete search history.

(56) References Cited

U.S. PATENT DOCUMENTS

| 2006/0156488 A1 | 7/2006 | David et al. |
| 2011/0056508 A1 | 3/2011 | Gross et al. |
| 2011/0146005 A1* | 6/2011 | Gross ........................ A61K 8/22 |
| | | 8/406 |

FOREIGN PATENT DOCUMENTS

| EP | 1672033 A2 | 6/2006 |
| GB | 1125619 A | 8/1968 |
| WO | 01/16273 | * 3/2001 |
| WO | 0116273 A1 | 3/2001 |
| WO | 2008025240 A1 | 3/2008 |
| WO | 09/043613 | * 4/2009 |
| WO | 2009043613 A1 | 4/2009 |
| WO | 2017/109183 A1 | 6/2017 |
| WO | 2017/109185 A1 | 6/2017 |

OTHER PUBLICATIONS

International Search Report for counterpart Application No. PCT/EP2016/082578, dated Feb. 22, 2017.
International Search Report for counterpart Application No. PCT/EP2016/082577, dated May 11, 2017.
Cannon, et al., "Polyphosphoric Acid in the Bischler-Napieralski Reaction," Journal of the American Pharmaceutical Association, Scientific Edition A8, XP009190223, vol. 47, 1958, pp. 353-355.
Copp, F.C. et al., "Two New Short-Acting Nondepolarizing Neuromusclar Blocking Agents," Experientia, Springer Basel AG, CH, vol. 28, No. 1, Jan. 1, 1972, pp. 47-48.
Hughes, R., "Evaluation of the Neuromuscular Blocking Properties and Side-Effects of the Two New Isoquinolinium Bisquaternary Compounds (BW.252C64 and BW.403C65)," British Journal of Anaesthesia, vol. 44, No. 27, Jan. 1, 1972, pp. 27-42.

(Continued)

*Primary Examiner* — D Margaret M Seaman
(74) *Attorney, Agent, or Firm* — The Marbury Law Group, PLLC

(57) ABSTRACT

The present invention relates to the use of one or more particular dihydroisoquinolinium salts of formula (I) for treating keratin materials, in particular keratin fibres, especially human keratin fibres such as the hair. The invention also relates to a process for treating keratin materials using said salts and optionally one or more chemical oxidizing agents. A subject of the invention is also a composition for lightening keratin materials, comprising one or more dihydroisoquinolinium salts and one or more chemical oxidizing agents. The present invention also relates to one or more particular dihydroisoquinolinium salts and also to compositions containing them, in particular compositions comprising a physiologically acceptable medium.

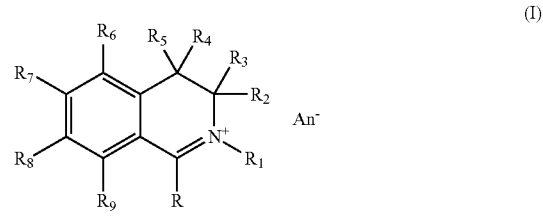

14 Claims, No Drawings

(56) References Cited

OTHER PUBLICATIONS

Stenlake, John B. et al., "Bis-3, 4-Dihydroisoquinolinium Salts as Potential Neuromuscular Blocking Agents," Chimica Therapeutique, Editions Dimeo, Arcueil, FR, vol. 16, No. 6, Jan. 1, 1981, pp. 503-507.

Szántay, Csaba et al., "Beiträge zur Chemie der Heterocyclishchen, Pseudobasischen Aminocarbinole, XXV. Redoxprozesse bei aus Bis-[3.4-dihydro-isochinolinium]-Salzen freisetzbaren Basen," Chemische Berichte, vol. 96, No. 7, Jul. 1, 1963, pp. 1779-1787 (translation not available).

International Search Report for Application No. PCT/EP2016/082580, dated Mar. 6, 2017.

Non-Final Office Action for copending U.S. Appl. No. 16/064,129, dated Dec. 3, 2020.

Non-Final Office Action for copending U.S. Appl. No. 16/064,256, dated Jul. 24, 2020.

Final Office Action for copending U.S. Appl. No. 16/064,256, dated Feb. 11, 2021.

Final Office Action for copending U.S. Appl. No. 16/064,129, dated Jun. 14, 2021.

\* cited by examiner

USE OF SUBSTITUTED DIHYDROISOQUINOLINIUM SALTS FOR TREATING KERATIN MATERIALS, COMPOSITIONS AND IMPLEMENTATION PROCESSES

CROSS REFERENCE TO RELATED APPLICATIONS

This is a national stage application of PCT/EP2016/082580, filed internationally on Dec. 23, 2016, which claims priority to French Application No. 1563276, filed on Dec. 23, 2015, both of which are incorporated by reference herein in their entireties.

The present invention relates to the use of one or more substituted dihydroisoquinolinium salts for treating keratin materials, in particular keratin fibres, especially human keratin fibres such as the hair. The invention also relates to a process for treating keratin materials using said salts and optionally in the presence of one or more chemical oxidizing agents.

A subject of the invention is also a composition for lightening keratin materials, comprising one or more substituted dihydroisoquinolinium salts as defined below and one or more chemical oxidizing agents.

The present invention also relates to one or more particular substituted dihydroisoquinolinium salts and also to compositions containing them, in particular compositions comprising a physiologically acceptable medium.

When a person wishes to change hair colour, in particular when she wishes to obtain a colour lighter than her original colour, it is often necessary to perform lightening or bleaching of the hair. To do this, lightening or bleaching products are used. This step is optionally combined with a hair colouring step.

It is known practice to lighten or bleach keratin materials, especially keratin fibres, and in particular human keratin fibres such as the hair, with lightening or bleaching compositions containing one or more chemical oxidizing agents.

Among the chemical oxidizing agents used conventionally, mention may be made of hydrogen peroxide, compounds that can produce hydrogen peroxide by hydrolysis, such as urea peroxide or persalts such as perborates, percarbonates and persulfates, hydrogen peroxide and persulfates being particularly preferred.

The role of the chemical oxidizing agent is to degrade the melanin of the hair, which, depending on the nature of the oxidizing agent and the pH conditions, leads to more or less pronounced lightening of the fibres.

The lightening or bleaching compositions are presented in anhydrous or aqueous form and in various different delivery forms: for example in the form of powders, creams, gels, foams or pastes, containing alkaline compounds such as alkaline amines or silicates, and a peroxygenated reagent such as ammonium or alkali metal persulfates, perborates or percarbonates, that are diluted at the time of use with an aqueous hydrogen peroxide composition.

The lightening bleaching compositions may also result from mixing, at the time of use, an anhydrous powder containing the peroxygenated reagent with an aqueous composition containing the alkaline compounds and another aqueous composition containing hydrogen peroxide.

Moreover, the keratin materials may also be bleached by means of a standard process involving applying to said materials an aqueous composition comprising at least one oxidizing agent.

Thus, for relatively mild lightening, the oxidizing agent is generally hydrogen peroxide. When greater lightening is desired, peroxygenated salts, for instance persulfates, are usually used in the presence of hydrogen peroxide.

To make a lightening or bleaching product for keratin materials that is more effective in terms of lightening and/or speed, it is currently necessary to combine hydrogen peroxide with an alkaline agent or persulfate salts with a basic pH to obtain adequate formation of active oxygen.

However, such a combination commonly causes degradation of the keratin materials, in particular keratin fibres, and may possibly lead to varying degrees of skin irritation.

Thus, there is a real need to use compounds which do not have the drawbacks mentioned above, i.e. which can produce, under safer conditions than for persulfates, powerful lightening of keratin materials, in particular of keratin fibres, while at the same time minimizing their degradation.

The Applicant has thus discovered, surprisingly, that the use of one or more substituted dihydroisoquinolinium salts of formula (I), as defined below, makes it possible especially to improve the oxidizing power of hydrogen peroxide, which allows greater lightening of keratin materials, in particular keratin fibres, while at the same time minimizing their degradation.

In other words, the use of the compounds of formula (I) according to the invention improves the activity of hydrogen peroxide without the need to increase its concentration or the need to use persulfate salts at high concentrations, which minimizes the problems of sensitization of keratin materials.

Thus, the use of the substituted dihydroisoquinolinium salt(s) according to the invention leads to greater lightening of keratin materials without, however, needing to increase the strength of the oxidizing agent.

In other words, the use of the substituted dihydroisoquinolinium salt(s) according to the invention makes it possible to boost the oxidizing activity of chemical oxidizing agents, especially hydrogen peroxide, leading to an improvement in the lightening of keratin materials relative to the use of the chemical oxidizing agent alone.

Furthermore, the dihydroisoquinolinium salts of formula (I) in combination with a chemical oxidizing agent, especially hydrogen peroxide, lead to more powerful lightening of the keratin materials than a chemical oxidizing agent alone.

A subject of the present invention is thus especially the use for treating keratin materials, preferably keratin fibres and skin, especially human keratin fibres such as the hair, of one or more compounds of formula (I), and also the addition salts thereof and the solvates thereof:

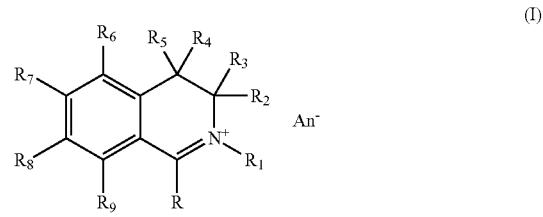

(I)

$An^-$
in which formula (I):
R represents:
a hydrogen atom,
a linear or branched $C_1$-$C_{12}$ alkyl radical optionally substituted with one or more groups, which may be identical or different, chosen from hydroxyl, $C_1$-$C_6$ alkoxy, cyano and amino —$NR_{10}R_{11}$ groups, $R_1$ represents:

a linear or branched $C_1$-$C_{12}$ alkyl radical optionally substituted with one or more groups, which may be identical or different, chosen from hydroxyl, $C_1$-$C_6$ alkoxy and amino —$NR_{10}R_{11}$ groups, $R_2$, $R_3$, $R_4$, $R_5$, $R_6$, $R_7$, $R_8$ and $R_9$ represent, independently of each other, a radical chosen from:

a hydrogen atom, a halogen atom, a linear or branched $C_1$-$C_6$ alkyl radical optionally substituted with one or more groups, which may be identical or different, chosen from hydroxyl, $C_1$-$C_6$ alkoxy and amino —$NR_{10}R_{11}$ groups, a $C_1$-$C_6$ alkoxy radical, a hydroxyl radical, an amino radical —$NR_{10}R_{11}$, an aminocarbonyl radical —$CONH_2$, $R_{10}$ and $R_{11}$, which may be identical or different, denote a hydrogen atom or a linear or branched $C_1$-$C_6$ alkyl radical, it being understood that R, $R_2$, $R_3$, $R_4$ and $R_5$ cannot be identical and correspond to a hydrogen atom, An– represents an organic or mineral anion or mixture of anions which ensures the electrical neutrality of the compounds of formula (I).

The compound(s) of formula (I) thus defined thus correspond to substituted dihydroisoquinolinium salts and act as oxidation activators.

The compound(s) of formula (I) according to the invention may be used in the presence of one or more chemical oxidizing agents for lightening keratin materials, preferably keratin fibres, in particular human keratin fibres such as the hair.

The present invention also relates to a process for treating keratin materials, preferably keratin fibres and skin, especially human keratin fibres such as the hair, which consists in applying to said materials one or more compounds of formula (I), and also the addition salts thereof and the solvates thereof.

Preferably, the process according to the invention consists in applying to keratin materials said compound(s) of formula (I) and one or more chemical oxidizing agents.

Moreover, a subject of the invention is a composition for lightening keratin materials, preferably keratin fibres and skin, especially human keratin fibres such as the hair, comprising one or more compounds of formula (I), and also the addition salts thereof and the solvates thereof, and one or more chemical oxidizing agents.

Similarly, the invention also relates to the use of said composition for lightening keratin materials, preferably keratin fibres and skin, especially human keratin fibres such as the hair.

In addition, the present invention relates to one or more particular compounds of formula (II), and also the addition salts and solvates thereof such as hydrates:

(II)

in which formula (II):

R represents:

a hydrogen atom, a linear or branched $C_1$-$C_{12}$ alkyl radical optionally substituted with one or more groups, which may be identical or different, chosen from hydroxyl, $C_1$-$C_6$ alkoxy, cyano and amino —$NR_{10}R_{11}$ groups, $R_1$ represents:

a linear or branched $C_1$-$C_{12}$ alkyl radical optionally substituted with one or more groups, which may be identical or different, chosen from hydroxyl, $C_1$-$C_6$ alkoxy and amino —$NR_{10}R_{11}$ groups, $R_2$, $R_3$, $R_4$, $R_5$, $R_6$, $R_7$, $R_8$ and $R_9$ represent, independently of each other, a radical chosen from:

a hydrogen atom, a halogen atom, a linear or branched $C_1$-$C_6$ alkyl radical optionally substituted with one or more groups, which may be identical or different, chosen from hydroxyl, $C_1$-$C_6$ alkoxy and amino —$NR_{10}R_{11}$ groups, an aminocarbonyl radical —$CONH_2$, $R_{10}$ and $R_{11}$, which may be identical or different, denote a hydrogen atom or a linear or branched $C_1$-$C_6$ alkyl radical, it being understood that R, $R_2$, $R_3$, $R_4$ and $R_5$ cannot be identical and correspond to a hydrogen atom, An⁻ represents an organic or mineral anion or mixture of anions which ensures the electrical neutrality of the compounds of formula (I), it being understood that formula (II) cannot represent the following compounds:

-continued

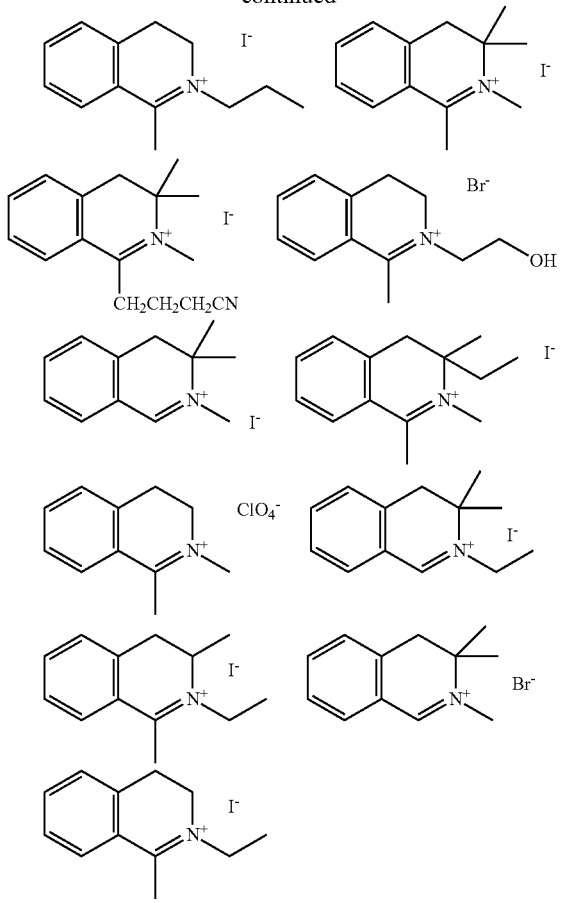

Similarly, another subject of the present invention relates to a composition comprising said compound(s) of formula (II), and also the addition salts thereof and the solvates thereof.

Other subjects, characteristics, aspects and advantages of the invention will emerge even more clearly on reading the description and the examples that follow.

In that which follows and unless otherwise indicated, the limits of a range of values are included within this range, in particular in the expressions "of between" and "ranging from . . . to . . . ".

Moreover, the expression "at least one" used in the present description is equivalent to the expression "one or more". In addition, the expression "at least two" is equivalent to the expression "two or more".

The term "anion or mixture of anions which ensures the electrical neutrality of the compounds of formulae (I) and (II)" means an anion or an anionic group derived from an organic or mineral acid salt which counterbalances the cationic charge of the compound; more particularly, the anionic counterion is chosen from: i) halides such as chloride or bromide; ii) nitrates; iii) sulfonates, including $C_1$-$C_6$ alkylsulfonates: Alk-S(O)$_2$O$^-$ such as methanesulfonate or mesylate and ethanesulfonate; iv) arylsulfonates: Ar—S(O)$_2$O$^-$ such as benzenesulfonate and toluenesulfonate or tosylate; v) citrate; vi) succinate; vii) tartrate; viii) lactate; ix) alkyl sulfates: Alk-O—S(O)O$^-$ such as methyl sulfate and ethyl sulfate; x) aryl sulfates: Alk-O—S(O)O$^-$ such as methyl sulfate and ethyl sulfate; x) aryl sulfates: Ar—O—S(O)O$^-$ such as benzene sulfate and toluene sulfate; xi) alkoxy sulfates: Alk-O—S(O)$_2$O$^-$ such as methoxy sulfate and ethoxy sulfate; xii) aryloxy sulfates: Ar—O—S(O)$_2$O$^-$, xiii) phosphates O=P(OH)$_2$—O$^-$, O=P(O$^-$)$_2$—OH O=P(O$^-$)$_3$, HO—[P(O)(O—)]w-P(O)(O$^-$)$_2$ with w being an integer; xiv) acetate; xv) triflate; and xvi) borates such as tetrafluoroborate, xvii) disulfate (O=)$_2$S(O$^-$)$_2$ or SO$_4^{2-}$ and monosulfate HSO$_4^-$, xviii) carbonate CO$_3^{2-}$ or hydrogen carbonate HCO$_3^-$; the anionic counterion, derived from the organic or mineral acid salt, ensures the electrical neutrality of the molecule: thus, it is understood that when the anion comprises several anionic charges, then the same anion can serve for the electrical neutrality of several cationic groups in the same molecule or else may serve for the electrical neutrality of several molecules.

The term "addition salts of the compounds of formulae (I) and (II) according to the invention" thus means addition salts with an organic or mineral acid, and addition salts with an organic or mineral base.

The addition salts of the compounds of formulae (I) and (II) according to the invention are in particular chosen from addition salts with an acid, such as hydrochlorides, hydrobromides, sulfates, citrates, succinates, tartrates, lactates, tosylates, benzenesulfonates, methanesulfonates, phosphates and acetates, and the addition salts with a base such as sodium hydroxide, potassium hydroxide, ammonia, amines or alkanolamines.

Moreover, the solvates of the compounds of formulae (I) and (II) according to the invention more particularly represent the hydrates of said compounds and/or the combination of said compounds with a linear or branched $C_1$ to $C_4$ alcohol such as methanol, ethanol, isopropanol or n-propanol. Preferably, the solvates are hydrates.

Use of the Compounds of Formula (I)

An– represents an organic or mineral anion or mixture of anions which ensures the electrical neutrality of the compounds of formula (I).

Preferably, An– is an anion chosen from halides, in particular chloride and bromide, sulfates, phosphates, carbonate, hydrogen carbonate, methanesulfonate, para-toluenesulfonate, camphorsulfonate, tartrate, citrate, lactate and acetate.

More preferentially, An– is an anion chosen from para-toluenesulfonate and halides, in particular chloride.

According to one embodiment, $R_4$, $R_5$, $R_6$ and $R_9$ are identical. In accordance with this embodiment, $R_4$, $R_5$, $R_6$ and $R_9$ are identical and preferably represent a hydrogen atom.

In accordance with this embodiment, $R_7$ and $R_8$ are preferably identical and represent a hydrogen atom or a $C_1$-$C_6$ alkoxy radical.

In accordance with this embodiment, $R_7$ and $R_8$ preferably represent a $C_1$-$C_6$ and preferentially C1 alkoxy radical.

Preferably, the compound(s) of formula (I) as defined above are chosen from the compound(s) of formula (II), and also the addition salts thereof and the solvates thereof:

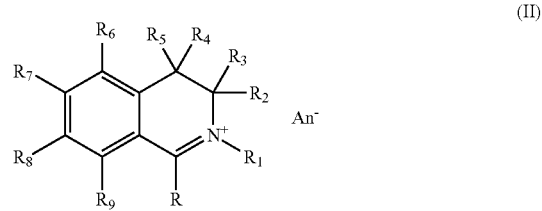

(II)

in which formula (II):

R represents:
- a hydrogen atom,
- a linear or branched $C_1$-$C_{12}$ alkyl radical optionally substituted with one or more groups, which may be identical or different, chosen from hydroxyl, $C_1$-$C_6$ alkoxy, cyano and amino —$NR_{10}R_{11}$ groups, $R_1$ represents:
- a linear or branched $C_1$-$C_{12}$ alkyl radical optionally substituted with one or more groups, which may be identical or different, chosen from hydroxyl, $C_1$-$C_6$ alkoxy and amino —$NR_{10}R_{11}$ groups, $R_2$, $R_3$, $R_4$, $R_5$, $R_6$, $R_7$, $R_8$ and $R_9$ represent, independently of each other, a radical chosen from:
- a hydrogen atom,
- a halogen atom,
- a linear or branched $C_1$-$C_6$ alkyl radical optionally substituted with one or more groups, which may be identical or different, chosen from hydroxyl, $C_1$-$C_6$ alkoxy and amino —$NR_{10}R_{11}$ groups,
- an aminocarbonyl radical —$CONH_2$, $R_{10}$ and $R_{11}$, which may be identical or different, denote a hydrogen atom or a linear or branched $C_1$-$C_6$ alkyl radical, it being understood that R, $R_2$, $R_3$, $R_4$ and $R_5$ cannot be identical and correspond to a hydrogen atom, An— represents an organic or mineral anion or mixture of anions which ensures the electrical neutrality of the compounds of formula (I).

According to one embodiment, R represents a linear or branched $C_1$-$C_{12}$ alkyl radical, optionally substituted with one or more groups, which may be identical or different, chosen from hydroxyl, $C_1$-$C_6$ alkoxy, cyano and amino —$NR_{10}R_{11}$ groups; $R_{10}$ and $R_{11}$ having the definition given previously in formula (I).

In accordance with this embodiment, R especially represents a linear or branched, in particular linear, $C_1$-$C_6$ alkyl radical.

According to another embodiment, R represents a hydrogen atom.

Preferably, R represents a linear or branched $C_1$-$C_{12}$ alkyl radical, optionally substituted with one or more groups, which may be identical or different, chosen from hydroxyl, $C_1$-$C_6$ alkoxy, cyano and amino —$NR_{10}R_{11}$ groups; $R_{10}$ and $R_{11}$ having the definition given previously in formula (I).

According to one embodiment, $R_1$ represents a linear or branched $C_1$-$C_{12}$ alkyl radical optionally substituted with one or more groups, which may be identical or different, chosen from hydroxyl, $C_1$-$C_6$ alkoxy and amino —$NR_{10}R_{11}$ groups.

Preferably, $R_1$ represents a linear or branched $C_1$-$C_{12}$, especially $C_1$-$C_6$, more preferentially $C_1$-$C_4$ and in particular $C_1$ alkyl radical.

According to one embodiment, $R_2$ and $R_3$ are identical.

According to another embodiment, $R_2$ and $R_3$, which may be identical or different, represent a hydrogen atom or a linear or branched, especially linear, $C_1$-$C_6$ alkyl radical, optionally substituted with one or more groups, which may be identical or different, chosen from hydroxyl, $C_1$-$C_6$ alkoxy and amino —$NR_{10}R_{11}$ groups; $R_{10}$ and $R_{11}$ having the definition given previously in formula (I).

Preferably, $R_2$ and $R_3$ are identical and represent a hydrogen atom or a linear or branched $C_1$-$C_6$ alkyl radical, optionally substituted with one or more groups, which may be identical or different, chosen from hydroxyl, $C_1$-$C_6$ alkoxy and amino —$NR_{10}R_{11}$ groups; $R_{10}$ and $R_{11}$ having the definition given previously in formula (I).

Preferentially, $R_2$ and $R_3$ are identical and represent a hydrogen atom or a linear $C_1$-$C_6$ and in particular $C_1$ alkyl radical.

According to one embodiment, $R_4$ and $R_5$ are identical.

In accordance with this embodiment, $R_4$ and $R_5$ are identical and preferably represent a hydrogen atom.

According to one embodiment, $R_6$, $R_7$, $R_8$ and $R_9$ are identical.

In accordance with this embodiment, $R_6$, $R_7$, $R_8$ and $R_9$ preferably represent a hydrogen atom.

According to one embodiment, $R_4$, $R_5$, $R_6$ and $R_9$ are identical. In accordance with this embodiment, $R_4$, $R_5$, $R_6$ and $R_9$ are identical and preferably represent a hydrogen atom.

In accordance with this embodiment, $R_7$ and $R_8$ are preferably identical and represent a hydrogen atom.

In other words, preferentially, $R_4$, $R_5$, $R_6$, $R_7$, $R_8$ and $R_9$ correspond to a hydrogen atom.

In accordance with this embodiment, $R_2$ and $R_3$ are preferably identical and represent a hydrogen atom or a linear or branched $C_1$-$C_6$ alkyl radical, optionally substituted with one or more groups, which may be identical or different, chosen from hydroxyl, $C_1$-$C_6$ alkoxy and amino —$NR_{10}R_{11}$ groups; $R_{10}$ and $R_{11}$ having the definition given previously in formula (I).

In accordance with this embodiment, R especially represents a linear or branched, in particular linear, $C_1$-$C_6$ alkyl radical.

In accordance with this embodiment, An⁻ is an anion preferentially chosen from para-toluenesulfonate and halides, in particular chloride.

The compound(s) of formula (I) are preferentially chosen from the following compounds:

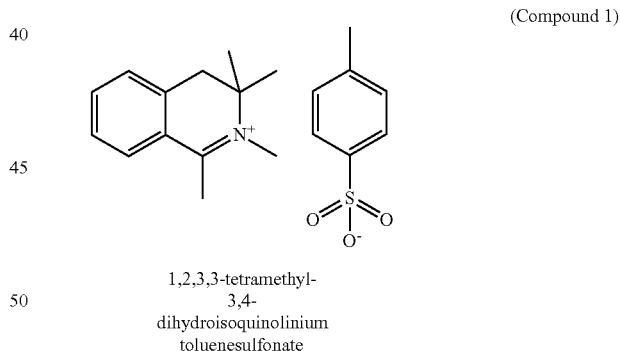

(Compound 1)

1,2,3,3-tetramethyl-
3,4-
dihydroisoquinolinium
toluenesulfonate

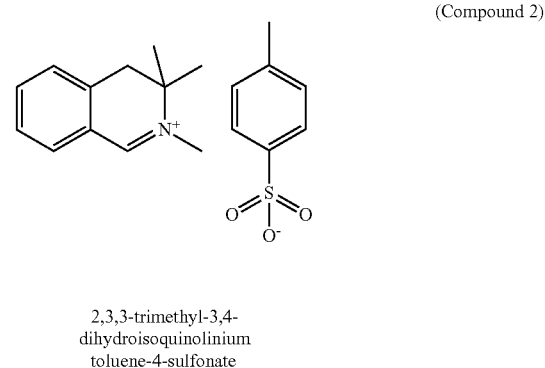

(Compound 2)

2,3,3-trimethyl-3,4-
dihydroisoquinolinium
toluene-4-sulfonate

-continued

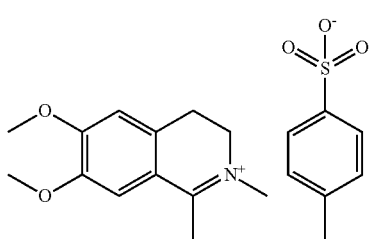

(Compound 3)

6,7-dimethoxy-1,2-dimethyl-,3,4-dihydroisoquinolinium toluene-4-sulfonate

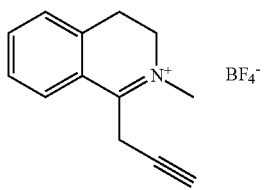

(Compound 4)

1-(cyanomethyl)-2-methyl-3,4-dihydroisoquinolinium tetrafluoroborate and also mixtures thereof.

As indicated previously, the compound(s) of formula (I) according to the invention, preferably compounds 1 to 4, may be used in the presence of one or more chemical oxidizing agents for lightening keratin materials, preferably keratin fibres, in particular human keratin fibres such as the hair.

The oxidizing agents are such as those described hereinafter.

Composition Containing Compounds of Formula (I)

Thus, the invention relates to a composition comprising the compound(s) of formula (I), preferably the compound(s) of formula (II), as defined above, and also the addition salts thereof and the solvates thereof, and one or more chemical oxidizing agents.

Preferably, the composition according to the invention comprises one or more compounds of formula (I) chosen from compounds 1 to 4.

The composition according to the invention lightens keratin materials, especially keratin fibres and preferably human keratin fibres such as the hair, using less chemical oxidizing agent.

According to a particular embodiment of the invention, the dye composition comprises at least one chemical oxidizing agent. The expression "chemical oxidizing agent" is understood to mean an oxidizing agent other than atmospheric oxygen. Preferentially, the composition of the invention contains one or more chemical oxidizing agents.

The oxidizing agent(s) used in the invention are for example hydrogen peroxide, urea peroxide, alkali metal bromates, persalts such as perborates and persulfates, peracids and oxidase enzymes, among which mention may be made of peroxidases, 2-electron oxidoreductases such as uricases, and 4-electron oxygenases, for instance laccases. Hydrogen peroxide is particularly preferred.

More particularly, the chemical oxidizing agent(s) are chosen from hydrogen peroxide, urea peroxide, alkali metal bromates, peroxygenated salts, for instance persulfates, perborates, peracids and precursors thereof and percarbonates of alkali metals or alkaline-earth metals. The chemical oxidizing agent(s) advantageously consist of hydrogen peroxide.

The compound(s) of formula (I), and also the addition salts thereof and the solvates thereof, may be present in the composition according to the invention in a content that may range from 0.01% to 10% by weight, preferably in a content ranging from 0.5% to 3% by weight, more preferably in a content ranging from 1% to 3% by weight relative to the total weight of the composition.

Preferentially, the chemical oxidizing agent is hydrogen peroxide.

According to one embodiment, the composition according to the invention comprises one or more compounds of formula (I), preferably of formula (II), and the addition salts and solvates thereof, and at least one chemical oxidizing agent such as hydrogen peroxide.

In accordance with this embodiment, the composition preferably additionally comprises one or more persulfates.

In other words, the composition may preferentially comprise a mixture of hydrogen peroxide and persulfates.

According to one embodiment, the composition according to the invention comprises one or more compounds of formula (I), preferably of formula (II), and the addition salts and solvates thereof, and hydrogen peroxide as chemical oxidizing agent; said composition being free of persulfates.

The chemical oxidizing agent(s) may be present in the composition according to the invention in a content that may range from 0.5 to 9% by weight of the ready-to-use composition, preferably in a content ranging from 1.5% to 9% by weight, relative to the total weight of the ready-to-use composition.

Preferably, the composition according to the invention may comprise one or more alkaline agents, especially organic or mineral alkaline agents.

The mineral alkaline agent(s) are preferably chosen from aqueous ammonia, ammonium halides, in particular ammonium chloride, alkali metal carbonates or bicarbonates such as sodium or potassium carbonates and sodium or potassium bicarbonates, sodium hydroxide or potassium hydroxide, or mixtures thereof.

The organic alkaline agent(s) are preferably chosen from organic amines with a pKb at 25° C. of less than 12, preferably less than 10.5. It should be noted that it is the pKb corresponding to the function of highest basicity. In addition, the organic amines do not comprise any alkyl or alkenyl fatty chain comprising more than ten carbon atoms.

The organic alkaline agent(s) are chosen, for example, from alkanolamines, oxyethylenated and/or oxypropylenated ethylenediamines, amino acids and the compounds of formula (III) below:

(III)

in which formula (III) W is a divalent $C_1$-$C_6$ alkylene radical optionally substituted with one or more hydroxyl groups or a $C_1$-$C_6$ alkyl radical, and/or optionally interrupted with one or more heteroatoms such as O, or —NRu; Rx, Ry, Rz, Rt and Ru, which may be identical or different, represent a hydrogen atom or a $C_1$-$C_6$ alkyl, $C_1$-$C_6$ hydroxyalkyl or $C_1$-$C_6$ aminoalkyl radical.

The term "alkanolamine" means an organic amine comprising a primary, secondary or tertiary amine function, and one or more linear or branched $C_1$ to $C_8$ alkyl groups bearing one or more hydroxyl radicals.

Organic amines chosen from alkanolamines such as monoalkanolamines, dialkanolamines or trialkanolamines comprising one to three identical or different $C_1$-$C_4$ hydroxyalkyl radicals are in particular suitable for performing the invention.

Among the compounds of this type, mention may be made of monoethanolamine (MEA), diethanolamine, triethanolamine, mono isopropanolamine, diisopropanolamine, N,N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethyl)aminomethane.

More particularly, the amino acids that may be used are of natural or synthetic origin, in their L, D or racemic form, and comprise at least one acid function chosen more particularly from carboxylic acid, sulfonic acid, phosphonic acid and phosphoric acid functions. The amino acids may be in neutral or ionic form.

As amino acids that may be used in the present invention, mention may be made in particular of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine and salts thereof.

Advantageously, the amino acids are basic amino acids comprising an additional amine function optionally included in a ring or in a ureido function.

Such basic amino acids are preferably chosen from those corresponding to formula (IV) below, and also the salts thereof

R—$CH_2$—CH($NH_2$)—C(O)—OH  (IV)

in which R represents a group chosen from imidazolyl, preferably imidazolyl-4-yl; aminopropyl; amino ethyl; —$(CH_2)_2$NH—C(O)—$NH_2$; and $(CH_2)_2$—NH—C(NH)—$NH_2$.

The organic amine may also be chosen from organic amines of heterocyclic type. Besides histidine that has already been mentioned in the amino acids, mention may in particular be made of pyridine, piperidine, imidazole, triazole, tetrazole and benzimidazole.

The organic amine may also be chosen from amino acid dipeptides. As amino acid dipeptides that may be used in the present invention, mention may be made especially of carnosine, anserine and balenine.

The organic amine may also be chosen from compounds comprising a guanidine function. As amines of this type that may be used in the present invention, besides arginine, which has already been mentioned as an amino acid, mention may be made especially of creatine, creatinine, 1,1-dimethylguanidine, 1,1-diethylguanidine, glycocyamine, metformin, agmatine, N-amidino alanine, 3-guanidinopropionic acid, 4-guanidinobutyric acid and 2-([amino(imino) methyl]amino)ethane-1-sulfonic acid.

Hybrid compounds that may be mentioned include the salts of the amines mentioned previously with acids such as carbonic acid or hydrochloric acid.

Guanidine carbonate or monoethanolamine hydrochloride may be used in particular.

Preferably, the alkaline agent(s) present in the composition according to the invention are chosen from aqueous ammonia, alkanolamines, amino acids in neutral or ionic form, in particular basic amino acids, and preferably corresponding to those of formula (IV).

More preferentially, the alkaline agent(s) present in the composition according to the invention are chosen from aqueous ammonia and alkanolamines, and mixtures thereof.

More preferentially, the alkaline agent(s) present in the composition according to the invention are chosen from aqueous ammonia and ammonium chloride.

According to a particular embodiment of the invention, the alkaline agent(s) are mineral.

According to one particular embodiment of the invention, the alkaline agent(s) are organic such as alkanolamines, particularly monoethanolamine.

The quantity of alkaline agent(s) present in the composition according to the invention may range from 0.01% to 30% by weight, and preferably from 0.1% to 20% by weight relative to the total weight of the composition.

The composition according to the invention has a pH greater than or equal to 4. Preferably, the pH of the composition according to the invention varies from 7 to 11, more preferentially from 8 to 10 and more preferentially from 8.5 to 9.5.

According to one embodiment, the composition according to the invention comprises one or more compounds of formula (II) and the addition salts and solvates thereof, one or more chemical oxidizing agents and one or more alkaline agents chosen from aqueous ammonia and ammonium halides such as ammonium chloride.

In accordance with this embodiment, the compound of formula (II) is preferably chosen from compounds 1, 2 and 4 as described above.

In accordance with this embodiment, the chemical oxidizing agent is preferably hydrogen peroxide.

The composition according to the invention may optionally comprise one or more additives, different from the compounds of the invention and among which mention may be made of organic solvents, cationic, anionic, nonionic or amphoteric polymers or mixtures thereof, antidandruff agents, anti-seborrhoea agents, agents for preventing hair loss and/or for promoting hair regrowth, vitamins and provitamins including panthenol, sunscreens, mineral or organic pigments, sequestrants, plasticizers, solubilizers, acidifying agents, mineral or organic thickeners, especially polymeric thickeners, opacifiers or nacreous agents, antioxidants, hydroxy acids, fragrances, preserving agents, pigments and ceramides.

Needless to say, those skilled in the art will take care to select this or these optional additional compound(s) such that the advantageous properties intrinsically associated with the composition according to the invention are not, or are not substantially, adversely affected by the envisaged addition(s).

The above additives may generally be present in an amount, for each of them, of between 0 and 20% by weight relative to the total weight of the composition.

The composition according to the invention preferentially comprises a physiologically acceptable medium.

For the purposes of the present invention, the term "physiologically acceptable medium" is intended to denote a medium that is suitable for the topical administration of a composition. A physiologically acceptable medium is preferentially a cosmetically or dermatologically acceptable medium, i.e. a medium that has no unpleasant odour or appearance, and that is entirely compatible with the topical administration route. In the present case, where the composition is intended for topical administration, that is to say for administration by application at the surface of the keratin material under consideration, such a medium is considered in particular to be physiologically acceptable when it does not cause stinging, tightness or redness unacceptable to the user.

Treatment Process According to the Invention

The process for treating keratin materials consists in applying to said materials one or more compounds of formula (I) as defined above optionally in the presence of one or more chemical oxidizing agents.

Preferably, the compound(s) of formula (I) according to the invention are applied in the presence of one or more chemical oxidizing agents, more preferentially hydrogen peroxide.

According to one embodiment, the treatment process consists in applying the composition as defined previously to keratin materials.

Preferably, the treatment process consists in applying the composition as defined previously on dry or wet keratin fibres. The composition is left in place on the fibres for a period, generally from 1 minute to 1 hour, preferably from 5 minutes to 30 minutes.

The temperature during the process is conventionally between room temperature (between 15 and 25° C.) and 80° C. and preferably between room temperature and 60° C.

Preferentially, the composition is applied at room temperature.

After the treatment, the keratin materials are optionally rinsed with water, optionally washed with a shampoo and then rinsed with water, before being dried or left to dry.

The composition according to the invention may be prepared by mixing at least two compositions.

The composition according to the invention may especially be obtained by mixing two compositions:
- a composition (A) comprising one or more compounds of formula (I) according to the invention, and
- a composition (B) comprising one or more chemical oxidizing agents.

Compounds of Formula (II) and Corresponding Composition

As indicated previously, the present invention also relates to compounds of formula (II) as defined previously, and also the addition salts thereof and the solvates thereof, it being understood that formula (II) cannot represent the compounds defined previously.

The invention also relates to a composition comprising one or more compounds of formula (II) as defined previously.

Preferably, the composition comprises one or more compounds of formula (II) chosen from compounds 1, 2 and 4 as described above.

The compound(s) of formula (II), and also the addition salts thereof and the solvates thereof, may be present in the composition according to the invention in a content that may range from 0.01% to 10% by weight, preferably in a content ranging from 0.5% to 2% by weight, relative to the total weight of the composition.

The composition preferentially comprises a physiologically acceptable medium.

Process for Preparing the Compounds of Formula (II)

The compounds of formula (II) may be obtained by quaternization of dihydroisoquinoline derivatives (1) with alkylating derivatives $R_1$-An (2) with An⁻ representing a leaving group such as a halogen atom, in particular chlorine, bromine and iodine, an alkylsulfonate or an arylsulfonate.

Such a reaction generally takes place in the presence of a polar protic solvent, for example ethanol, and may be performed at room temperature (27° C.) and is accelerated by heating (at solvent reflux).

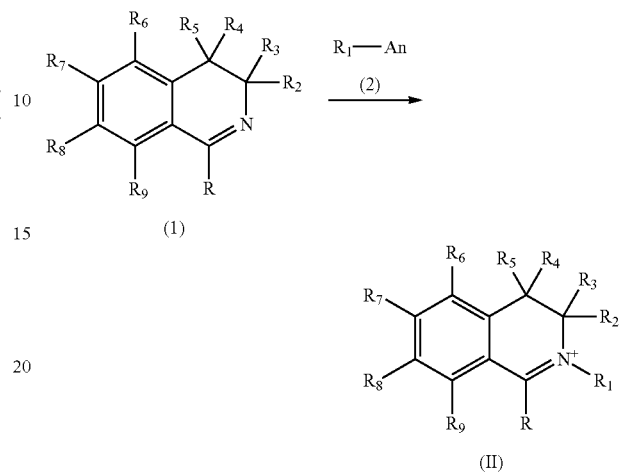

The compounds of formula (II) may also be obtained by simply exchanging the counter-anion:

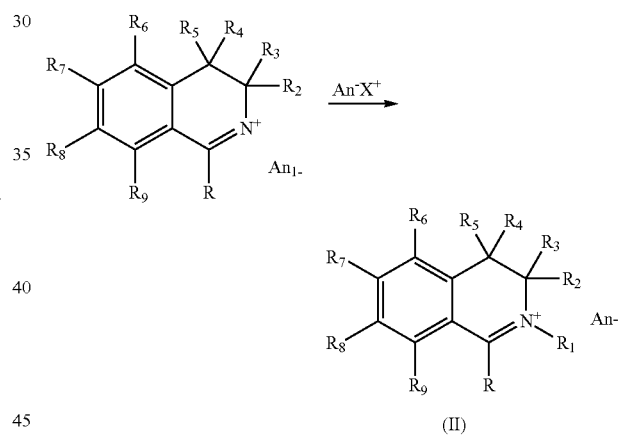

More generally, the compounds of formula (II) may be obtained by drawing on the bibliographic references below: Archiv der Pharmazie (Weinheim, Germany), 1988, vol. 321, pages 759-764, Journal of Organic Chemistry, 2014, vol. 10, pages 2981-2988, Tetrahedron, 2012, vol. 68, 26 pages 5137-5144, Heterocycles, 2004, vol. 63, 2 pages 401-409, Green Chemistry, 2014, vol. 16, 10 pages 4524-4529, Journal of Organic Chemistry, 1982, vol. 47, 12 pages 2308-2312, Tetrahedron, 1993, vol. 49, 2 pages 423-438, Synthesis, 1992, 9 pages 887-890, Journal of the American Chemical Society, 1949, vol. 71, pages 3405, 3407, Tetrahedron Letters, 1987, vol. 28, 48 pages 6061-6064.

The present invention also relates to the use of one or more compounds of formula (I) as defined previously, as oxidation activator.

In particular, the compound(s) of formula (I) according to the invention are used in the presence of one or more chemical oxidizing agents for improving the lightening of keratin materials, especially keratin fibres, preferably human keratin fibres such as the hair.

In other words, the compound(s) of formula (I) according to the invention are used for improving the oxidizing activity of one or more chemical oxidizing agents.

Preferably, the chemical oxidizing agent is hydrogen peroxide.

The examples that follow serve to illustrate the invention without, however, being limiting in nature.

In these examples, the colour of the locks was evaluated in the CIE L*a*b* system, using a Minolta Spectrophotometer CM2600D colorimeter.

In this L*a*b* system, the three parameters denote, respectively, the colour intensity (L*), the green/red colour axis (a*) and the blue/yellow colour axis (b*). The higher the value of L*, the lighter the colour. The higher the value of a*, the redder the colour and the higher the value of b*, the yellower the colour.

EXAMPLES

Example 1

Synthesis of 1,2,3,3-tetramethyl-3,4-dihydroisoquinolinium toluene-4-sulfonate (Compound 1)

(1)

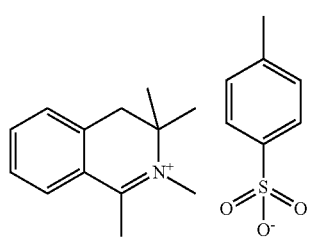

Step 1: Synthesis of 1,3,3-trimethyl-3,4-dihydroisoquinoline (a)

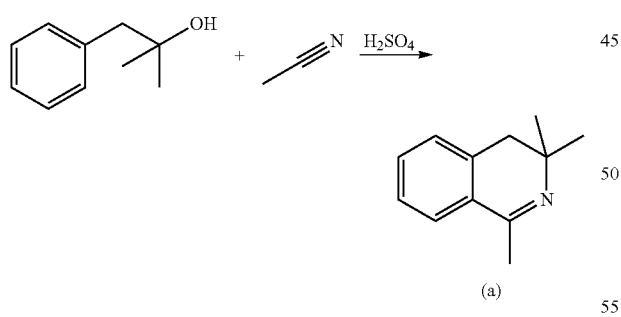

100.6 ml of concentrated sulfuric acid (9.4 eq.) are placed in a 500 ml three-necked flask equipped with a condenser and a thermometer, followed by cooling to a temperature in the region of 5-10° C. A mixture containing 30 g of methyl-1-phenyl-2-propanol (1 eq.) and 9.83 g of acetonitrile (1 eq.) is added dropwise. The mixture is stirred for 5 minutes at a temperature in the region of 5-10° C. and then for 5 hours at room temperature (monitoring by TLC, 95/5 $CH_2Cl_2$/MeOH).

The mixture is then poured into 1 litre of water and extracted with 100 ml of toluene. The aqueous phase is basified to pH 8.5 with ammonium carbonate and then extracted twice with 500 ml of MTBE (methyl tert-butyl ether). The organic phase is dried over $Na_2SO_4$, filtered, evaporated to dryness and then dried under vacuum over $P_2O_5$.

27 g (78% yield) of compound (a) are obtained in the form of a yellow liquid.

The NMR and mass analyses are in accordance with the expected structure.

Step 2: Synthesis of 1,2,3,3-tetramethyl-3,4-dihydroisoquinolinium toluene-4-sulfonate (1)

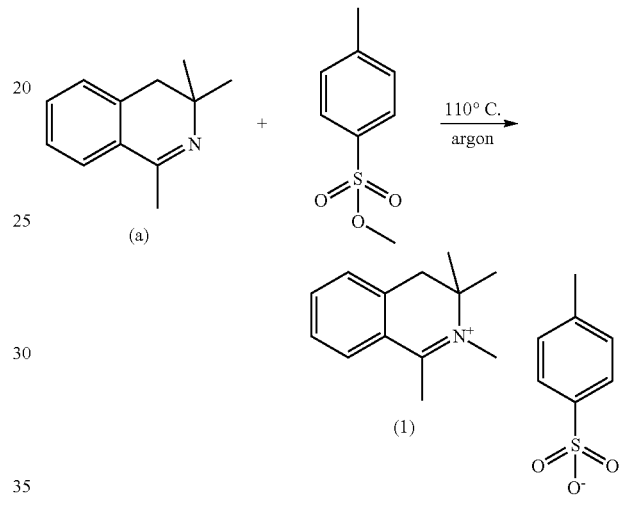

13 g of 1,3,3-trimethyl-3,4-dihydroisoquinoline (a) (1 eq.) and 14.25 g (1.02 eq.) of para-toluenesulfonyl methyl ester are placed in a 100 ml three-necked flask. The mixture is heated under argon at a temperature of 110° C. for 24 hours.

The resulting crude product is then purified on a column of silica, and 17.5 g of 1,2,3,3-tetramethyl-3,4-dihydroisoquinolinium toluene-4-sulfonate (1) are obtained (yield=65%).

The NMR and mass analyses are in accordance with the expected structure.

Example 2

Synthesis of 2,3,3-trimethyl-3,4-dihydroisoquinolinium toluene-4-sulfonate (Compound 2)

(2)

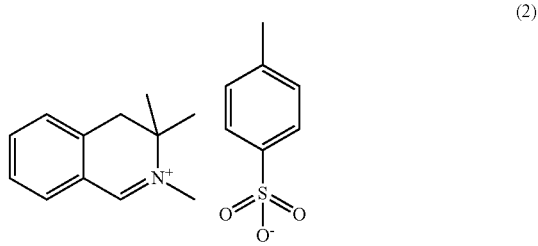

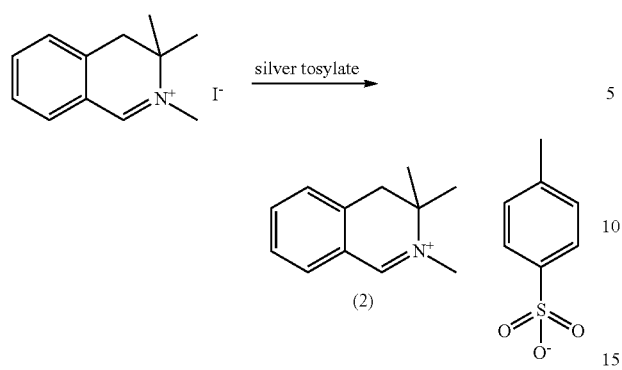

26.98 g of 2,3,3-trimethyl-3,4-dihydroisoquinolinium iodide (1 eq.) are placed in 250 ml of demineralized water in a 500 ml three-necked flask equipped with a condenser and a thermometer.

25 g of silver tosylate (1 eq.) are then added, protected from light. The mixture is left overnight at room temperature (monitoring by TLC, 95/5 CH$_2$Cl$_2$/MeOH).

A yellow precipitate is filtered off. The filtrate is evaporated to dryness and the oil crystallizes once dried under vacuum over P$_2$O$_5$. 6.2 g (100% yield) of compound 2 are obtained in the form of a hardening yellow oil.

The NMR and mass analyses are in accordance with the expected structure.

Example 3

Synthesis of 6,7-dimethoxy-1,2-dimethyl-3,4-dihydroisoquinolinium toluene-4-sulfonate (Compound 3)

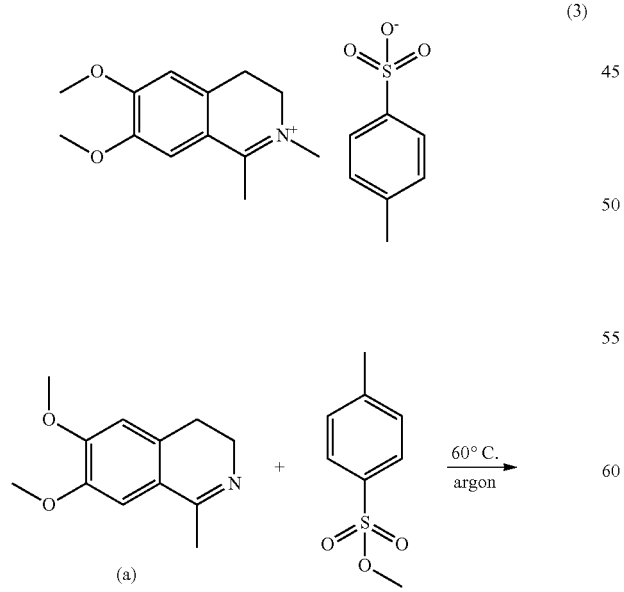

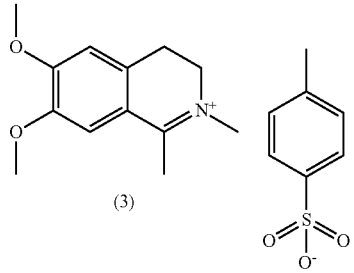

20 g of 1-methyl-6,7-dimethoxy-3,4-dihydroisoquinoline (1 eq.) and 18.5 g (1.02 eq.) of para-toluenesulfonyl methyl ester are placed in 70 ml of toluene in a 100 ml three-necked flask. The mixture is heated under argon at a temperature of 60° C. for 4 hours. A brown precipitate is filtered off and washed with acetone. 3.4 g (98% yield) of compound (3) are obtained in the form of a yellow powder.

The NMR and mass analyses are in accordance with the expected structure.

Example 4

Synthesis of 1-(cyanomethyl)-2-methyl-3,4-dihydroisoquinolinium tetrafluoroborate (Compound 4)

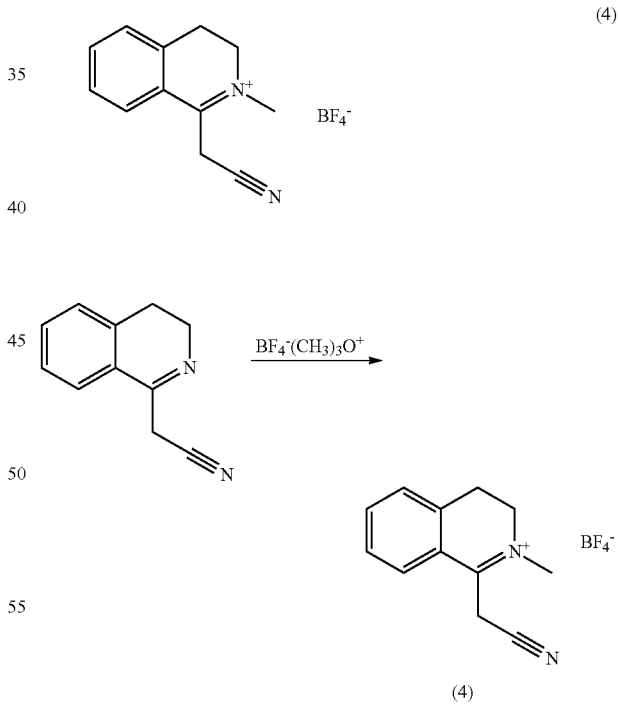

4.78 g (1.1 eq.) of trimethyloxonium tetrafluoroborate (Meerwein's salt) are placed in 80 ml of dichloromethane in a 100 ml three-necked flask. The mixture is cooled to a temperature of 0° C. A solution containing 5 g of 1-(cyanomethyl)-2-methyl-3,4-dihydroisoquinoline (1 eq.) in 50 ml of dichloromethane is then added dropwise. The reaction medium is then left at room temperature for 2 days. A yellow precipitate is filtered off and washed with diisopropyl ether. 5.05 g (63% yield) of compound (4) are obtained in the form of a yellow powder.

The NMR and mass analyses are in accordance with the expected structure.

Examples of Compositions and Evaluation

Example 5

In this example, the effect of improving the oxidizing power afforded by the dihydroisoquinolinium salts according to the invention is studied.

I. Preparation of Synthetic Melanin

The synthetic melanin used for the evaluation is obtained by polymerizing 5,6-dihydroxyindole with hydrogen peroxide according to the following procedure:

100 g of 5,6-dihydroxyindole are placed in 456 g of water heated to a temperature of 80° C. After stirring for 10 minutes, 1 ml of 20% aqueous ammonia solution is added and the medium is then maintained for 30 minutes at a temperature of 80° C. 152 g of 30% hydrogen peroxide are then added dropwise and stirring is continued for 2.5 hours at 80° C. After cooling, the suspension formed is filtered and washed with water.

86 g of synthetic melanin are thus obtained.

II. Compositions Tested

The compositions used in this example were obtained from the following ingredients (the percentages indicated are weight percentages relative to the total weight of the composition).

Compositions B and C are compositions according to the invention.

|  | Composition A | Composition B | Composition C |
|---|---|---|---|
| $H_2O_2$ | 1 ml | 1 ml | 1 ml |
| 1,2,3,3-Tetramethyl-3,4-dihydroisoquinolinium toluene-4-sulfonate (compound 1) | — | 60 mg | — |
| 2,3,3-Trimethyl-3,4-dihydroisoquinolinium toluene-4-sulfonate (compound 2) | — | — | 40.5 mg |
| Water | qs 100 | qs 100 | qs 100 |

III. Procedure

The following procedure is applied for each composition described in the table in section II.

1 ml of water, 1 ml of buffer of aqueous ammonia and ammonium chloride at pH 9.5 and 1 ml of the studied composition (compositions A, B and C) are applied to 1 mg of synthetic melanin obtained in accordance with section I.

The lightening (L*) obtained after 20 minutes of incubation at a temperature of 22° C. followed by 30 minutes at a temperature of 30° C. is measured using a Biotec Power Wave 200 spectrocolorimeter.

IV. Results

|  | Composition A | Composition B | Composition C |
|---|---|---|---|
| Lightening (L*) | 56 | 79 | 80 |

It is noted that greater lightening is obtained with compositions B and C according to the invention than with composition A.

In particular, it is noted that the presence of the dihydroisoquinolinium salts makes it possible to improve the oxidizing power of hydrogen peroxide and thus to boost its activity (comparison between composition A and compositions B-C according to the invention).

Example 6

I. Compositions Tested

Composition (A) and oxidizing composition (B) have been prepared from the following ingredients (the percentages indicated are percentages by weight relative to the total weight of the composition).

Composition (A):

| 2-Octyldodecanol | 11.5 |
|---|---|
| Laureth-2 | 3 |
| Polysorbate 21 | 11 |
| Mineral oil/Paraffinum liquidum | 74.5 |

Oxidizing Composition (B):

| GLYCERIN | 0.5 |
|---|---|
| TRIDECETH-2 CARBOXAMIDE MEA | 0.85 |
| TETRASODIUM PYROPHOSPHATE | 0.02 |
| HYDROGEN PEROXIDE (50%) | 12 |
| SODIUM STANNATE | 0.04 |
| PENTASODIUM PENTETATE (40% in water) | 0.15 |
| CETEARYL ALCOHOL/CETEARETH-25 (80/20) | 2.85 |
| WATER | Qsp 100 |

Compositions 1 (comparative) and 2 (invention) below were prepared by mixing 1 g of composition A, 1.5 g of the oxidizing composition B and by adding dihydroisoquinolinium dyes to be compared.

|  | Composition 1 (comparative) | Composition 2 (invention) |
|---|---|---|
| 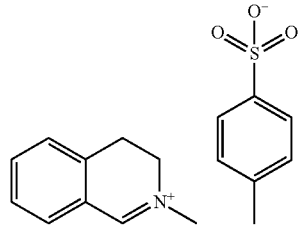<br>2-methyl-3,4-dihydroisoquinolinium 4-methylbenzenesulfonate | 30 mg | — |
| 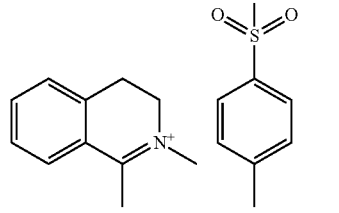<br>1,2-dimethyl-3,4-dihydroisoquinolinium 4-methylbenzenesulfonate | — | 30 mg |

-continued

|  | Composition 1 (comparative) | Composition 2 (invention) |
|---|---|---|
| Composition (A) | 1 g | 1 g |
| Oxidizing composition (B) | 1.5 g | 1.5 g |
| Aqueous ammonia 20% NH$_4$OH | Qs pH = 9.5 | Qs pH = 9.5 |

II. Procedure

After their preparation, compositions 1 and 2 are applied to natural 250 mg locks with a tone depth of 4. After a leave-on time of 30 minutes at a temperature of 27° C., the locks are washed, shampooed and dried.

The lightening is measured using the CIE L*a*b* system with a Minolta CM-3610d Spectrophotometer (illuminant D65, angle 10°, specular component included). According to this system, L* indicates the lightness of the hair.

The lightening is represented by the L*value: the higher the L* is, the better the lightening is.

III. Results

The results are summarized below:

|  | Composition 1 comparative | Composition 2 invention |
|---|---|---|
| Lightness (L*) | 24.7 | 27.3 |

The results show that composition 2 according to the invention exhibits a better lightening than composition 1 (comparative).

The invention claimed is:

1. A method for treating keratin materials comprising applying to said keratin materials, optionally in the presence of one or more chemical oxidizing agents, at least one compound chosen from:
(a) compounds of formula (I), the addition salts thereof, or the solvates thereof:

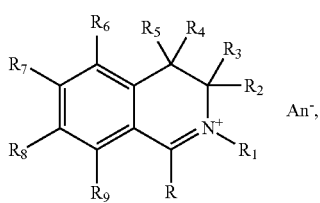

wherein in formula (I):
R is chosen from:
a linear or branched $C_1$-$C_{12}$ alkyl radical optionally substituted with at least one group, which may be identical or different, chosen from hydroxyl, $C_1$-$C_6$ alkoxy, cyano, or amino —NR$_{10}$R$_{11}$ groups;
R$_1$ is chosen from:
a linear or branched $C_1$-$C_{12}$ alkyl radical optionally substituted with at least one group, which may be identical or different, chosen from hydroxyl, $C_1$-$C_6$ alkoxy, or amino —NR$_{10}$R$_{11}$ groups;
R$_2$, R$_3$, R$_4$, R$_5$, R$_6$, R$_7$, R$_8$ and R$_9$, are chosen from, independently of each other, a radical chosen from:
a hydrogen atom,
a halogen atom,
a linear or branched $C_1$-$C_6$ alkyl radical optionally substituted with at least one group, which may be identical or different, chosen from hydroxyl, $C_1$-$C_6$ alkoxy, or amino —NR$_{10}$R$_{11}$ groups,
a $C_1$-$C_6$ alkoxy radical,
a hydroxyl radical,
an amino radical —NR$_{10}$R$_{11}$, or
an aminocarbonyl radical —CONH$_2$;
R$_{10}$ and R$_{11}$, which may be identical or different, are chosen from a hydrogen atom or a linear or branched $C_1$-$C_6$ alkyl radical;
with the proviso that R, R$_2$, R$_3$, R$_4$ and R$_5$ cannot all be identical; and
An$^-$ represents an organic or mineral anion or mixture of anions which ensures the electrical neutrality of the compounds of formula (I); or
(b) 2,3,3-trimethyl-3,4-dihydroisoquinolinium toluene-4-sulfonate (Compound 2):

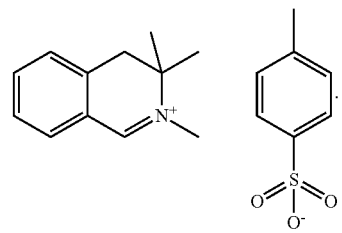

2. The method according to claim 1, wherein R$_4$, R$_5$, R$_6$ and R$_9$ are identical and represent a hydrogen atom.

3. The method according to claim 1, wherein R$_7$ and R$_8$ are identical and represent a hydrogen atom or a $C_1$-$C_6$ alkoxy radical.

4. The method according to claim 1, wherein the compound of formula (I) is chosen from the compounds of formula (II), the addition salts thereof, or the solvates thereof:

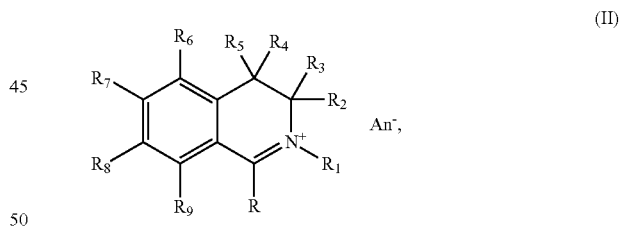

wherein in formula (II):
R is chosen from:
a linear or branched $C_1$-$C_{12}$ alkyl radical optionally substituted with at least one group, which may be identical or different, chosen from hydroxyl, $C_1$-$C_6$ alkoxy, cyano, or amino —NR$_{10}$R$_{11}$ groups;
R$_1$ is chosen from:
a linear or branched $C_1$-$C_{12}$ alkyl radical optionally substituted with at least one group, which may be identical or different, chosen from hydroxyl, $C_1$-$C_6$ alkoxy, or amino —NR$_{10}$R$_{11}$ groups;
R$_2$, R$_3$, R$_4$, R$_5$, R$_6$, R$_7$, R$_8$ and R$_9$ are chosen from, independently of each other, a radical chosen from:
a hydrogen atom,
a halogen atom, a linear or branched $C_1$-$C_6$ alkyl radical optionally substituted with at least one group, which may be identical or different, chosen from hydroxyl, $C_1$-$C_6$ alkoxy, or amino —$NR_{10}R_{11}$ groups, or an aminocarbonyl radical —$CONH_2$;

$R_{10}$ and $R_{11}$, which may be identical or different, are chosen from a hydrogen atom or a linear or branched $C_1$-$C_6$ alkyl radical;

with the proviso that R, $R_2$, $R_3$, $R_4$ and $R_5$ cannot all be identical; and An⁻ represents an organic or mineral anion or mixture of anions which ensures the electrical neutrality of the compounds of formula (II).

5. The method according to claim 4, wherein $R_2$ and $R_3$ are identical and represent a hydrogen atom or a linear or branched $C_1$-$C_6$ alkyl radical, optionally substituted with at least one group, which may be identical or different, chosen from hydroxyl, $C_1$-$C_6$ alkoxy, or amino —$NR_{10}R_{11}$ groups.

6. The method according to claim 4, wherein $R_4$ and $R_5$ are identical and represent a hydrogen atom.

7. The method according to claim 4, wherein $R_6$, $R_7$, $R_8$ and $R_9$ are identical and represent a hydrogen atom.

8. The method according to claim 1, wherein the compound of formula (I) is chosen from the following compounds:

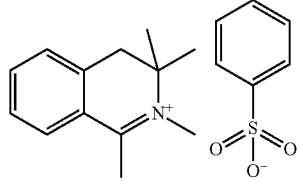

1,2,3,3-tetramethyl-3,4-dihydroisoquinolinium toluenesulfonate (Compound 1)

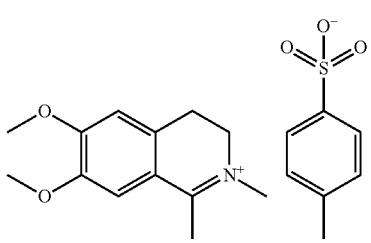

6,7-dimethoxy-1,2-dimethyl-,3,4-dihydroisoquinolinium toluene-4-sulfonate (Compound 3)

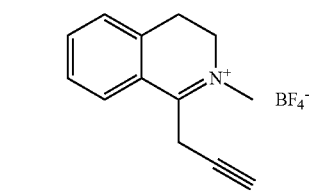

1-(cyanomethyl)-2-methyl-3,4-dihydroisoquinolinium tetrafluoroborate (Compound 4)

or mixtures thereof.

9. A method for improving the oxidizing activity of at least one chemical oxidizing agent, the method comprising combining at least one chemical oxidizing agent with a compound chosen from:

(a) compounds of formula (I), the addition salts thereof, or the solvates thereof:

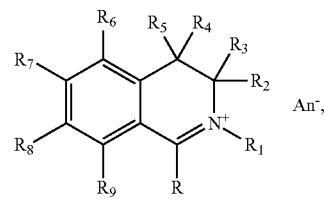

wherein in formula (I):

R is chosen from:
  a linear or branched $C_1$-$C_{12}$ alkyl radical optionally substituted with at least one group, which may be identical or different, chosen from hydroxyl, $C_1$-$C_6$ alkoxy, cyano, or amino —$NR_{10}R_{11}$ groups;

$R_1$ is chosen from:
  a linear or branched $C_1$-$C_{12}$ alkyl radical optionally substituted with at least one group, which may be identical or different, chosen from hydroxyl, $C_1$-$C_6$ alkoxy, or amino —$NR_{10}R_{11}$ groups;

$R_2$, $R_3$, $R_4$, $R_5$, $R_6$, $R_7$, $R_8$ and $R_9$, are chosen from, independently of each other, a radical chosen from:
  a hydrogen atom,
  a halogen atom,
  a linear or branched $C_1$-$C_6$ alkyl radical optionally substituted with at least one group, which may be identical or different, chosen from hydroxyl, $C_1$-$C_6$ alkoxy, or amino —$NR_{10}R_{11}$ groups,
  a $C_1$-$C_6$ alkoxy radical,
  a hydroxyl radical,
  an amino radical —$NR_{10}R_{11}$, or
  an aminocarbonyl radical —$CONH_2$;

$R_{10}$ and $R_{11}$, which may be identical or different, are chosen from a hydrogen atom or a linear or branched $C_1$-$C_6$ alkyl radical;

with the proviso that R, $R_2$, $R_3$, $R_4$ and $R_5$ cannot all be identical; and An⁻ represents an organic or mineral anion or mixture of anions which ensures the electrical neutrality of the compounds of formula (I); or (b) 2,3,3-trimethyl-3,4-dihydroisoquinolinium toluene-4-sulfonate (Compound 2):

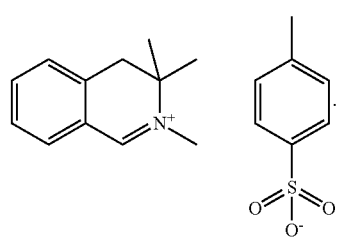

10. A composition comprising:
at least one chemical oxidizing agent, and
at least one compound;
wherein the at least one compound is chosen from:
(a) compounds of formula (I), the addition salts thereof, or the solvates thereof:

(I)

wherein in formula (I):
R is chosen from:
  a linear or branched $C_1$-$C_{12}$ alkyl radical optionally substituted with at least one group, which may be identical or different, chosen from hydroxyl, $C_1$-$C_6$ alkoxy, cyano, or amino —$NR_{10}R_{11}$ groups;
$R_1$ is chosen from:
  a linear or branched $C_1$-$C_{12}$ alkyl radical optionally substituted with at least one group, which may be identical or different, chosen from hydroxyl, $C_1$-$C_6$ alkoxy, or amino —$NR_{10}R_{11}$ groups;
$R_2$, $R_3$, $R_4$, $R_5$, $R_6$, $R_7$, $R_8$ and $R_9$, are chosen from, independently of each other, a radical chosen from:
  a hydrogen atom,
  a halogen atom,
  a linear or branched $C_1$-$C_6$ alkyl radical optionally substituted with at least one group, which may be identical or different, chosen from hydroxyl, $C_1$-$C_6$ alkoxy, or amino —$NR_{10}R_{11}$ groups,
  a $C_1$-$C_6$ alkoxy radical,
  a hydroxyl radical,
  an amino radical —$NR_{10}R_{11}$, or
  an aminocarbonyl radical —$CONH_2$;
$R_{10}$ and $R_{11}$, which may be identical or different, are chosen from a hydrogen atom or a linear or branched $C_1$-$C_6$ alkyl radical;
with the proviso that R, $R_2$, $R_3$, $R_4$ and $R_5$ cannot all be identical; and
An⁻ represents an organic or mineral anion or mixture of anions which ensures the electrical neutrality of the compounds of formula (I); or
(b) 2,3,3-trimethyl-3,4-dihydroisoquinolinium toluene-4-sulfonate (Compound 2):

11. The composition according to claim 10, wherein the at least one chemical oxidizing agent is hydrogen peroxide.

12. A compound chosen from:
(a) compounds of formula (II), the addition salts thereof, or the solvates thereof:

(II)

wherein in formula (II):
R is chosen from:
  a linear or branched $C_1$-$C_{12}$ alkyl radical optionally substituted with at least one group, which may be identical or different, chosen from hydroxyl, $C_1$-$C_6$ alkoxy, cyano, or amino —$NR_{10}R_{11}$ groups;
$R_1$ is chosen from:
  a linear or branched $C_1$-$C_{12}$ alkyl radical optionally substituted with at least one group, which may be identical or different, chosen from hydroxyl, $C_1$-$C_6$ alkoxy, cyano, or amino —$NR_{10}R_{11}$ groups;
$R_2$, $R_3$, $R_4$, $R_5$, $R_6$, $R_7$, $R_8$ and $R_9$ are chosen from, independently of each other, a radical chosen from:
  a hydrogen atom,
  a halogen atom,
  a linear or branched $C_1$-$C_6$ alkyl radical optionally substituted with at least one group, which may be identical or different, chosen from hydroxyl, $C_1$-$C_6$ alkoxy, or amino —$NR_{10}R_{11}$ groups, or
  an aminocarbonyl radical —$CONH_2$;
$R_{10}$ and $R_{11}$, which may be identical or different, are chosen from a hydrogen atom or a linear or branched $C_1$-$C_6$ alkyl radical;
with the proviso that R, $R_2$, $R_3$, $R_4$ and $R_5$ cannot all be identical; and
An⁻ represents an organic or mineral anion or mixture of anions which ensures the electrical neutrality of the compounds of formula (II);
or
(b) 2,3,3-trimethyl-3,4-dihydroisoquinolinium toluene-4-sulfonate (Compound 2):

wherein the compound is not chosen from the following compounds:

-continued

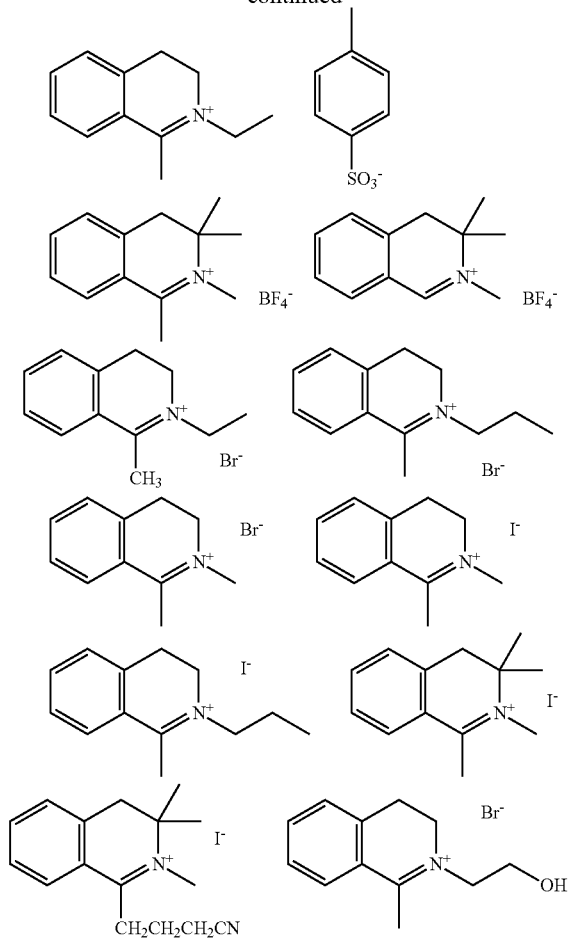

13. The compounds of formula (II) according to claim 12, chosen from 1,2,3,3-tetramethyl-3,4-dihydroisoquinolinium toluenesulfonate, 6,7-dimethoxy-1,2-dimethyl-,3,4-dihydroisoquinolinium toluene-4-sulfonate, or 1-(cyanomethyl)-2-methyl-3,4-dihydroisoquinolinium tetrafluoroborate.

14. A composition comprising at least one compound according to claim 12, the addition salts thereof, or the solvates thereof.

* * * * *